US012806381B2

(12) United States Patent
Isaacson et al.

(10) Patent No.: US 12,806,381 B2
(45) Date of Patent: Nov. 24, 2026

(54) METHOD AND APPARATUS FOR INTRODUCING A NEEDLE FOR CATHETER PLACEMENT

(71) Applicant: Becton, Dickinson and Company, Franklin Lakes, NJ (US)

(72) Inventors: Shawn Ray Isaacson, Layton, UT (US); Weston Finch Harding, Lehi, UT (US); Jeffrey O'Bryan, Murray, UT (US); Ralph Lee Sonderegger, Farmington, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 166 days.

(21) Appl. No.: 16/054,505

(22) Filed: Aug. 3, 2018

(65) Prior Publication Data

US 2019/0038877 A1 Feb. 7, 2019

Related U.S. Application Data

(60) Provisional application No. 62/541,158, filed on Aug. 4, 2017.

(51) Int. Cl.
*A61M 25/06* (2006.01)
*A61B 17/34* (2006.01)

(52) U.S. Cl.
CPC ..... *A61M 25/0606* (2013.01); *A61B 17/3415* (2013.01); *A61M 25/065* (2013.01);
(Continued)

(58) Field of Classification Search
CPC ............ A61M 5/3286; A61M 25/0606; A61M 25/065; A61M 25/0618; A61M 25/0643;
(Continued)

(56) References Cited

U.S. PATENT DOCUMENTS 2,697,438 A * 12/1954 Hickey ............... A61M 5/3286 604/274
3,090,384 A * 5/1963 Baldwin ............. A61M 5/3286 604/272

(Continued)

FOREIGN PATENT DOCUMENTS

EP 0 893 137 A2 1/1999
JP 2008-043445 A 2/2008

(Continued)

OTHER PUBLICATIONS

International Search Report and Written Opinion dated Jan. 8, 2019, which issued in the corresponding PCT Patent Application No. PCT/US2018/045108.

(Continued)

*Primary Examiner* — Kevin C Sirmons
*Assistant Examiner* — Leah J Swanson
(74) *Attorney, Agent, or Firm* — Dickinson Wright, PLLC

(57) ABSTRACT

A catheter assembly and method for introducing a needle to positioning a catheter, such as a peripheral IV catheter into a patient includes piercing a vein with a needle that extends from the distal end of the catheter. The needle has a distal tip that pierces the vein at an angle to penetrate a vein with a reduced incidence of transfixing, injury of the inner surface of the vein or inadvertently passing through side wall of the vein. The distal tip of the needle is introduced into the lumen of the vein at an incline where the distal tip is spaced from an inner surface of the vein and a bevel surface of the distal tip faces the inner surface of the vein opposite the entry point of the needle into the vein. A catheter is advanced from the distal tip of the needle into the lumen of the vein.

16 Claims, 10 Drawing Sheets

(52) U.S. Cl.
CPC ...... *A61B 17/3401* (2013.01); *A61M 25/0618* (2013.01); *A61M 25/0693* (2013.01)

(58) Field of Classification Search
CPC ........... A61M 25/0693; A61B 17/3401; A61B 17/3415
See application file for complete search history.

(56) References Cited

U.S. PATENT DOCUMENTS

| | | | | | |
|---|---|---|---|---|---|
| 3,308,822 | A * | 3/1967 | De Luca | A61M 5/3286 | 604/274 |
| 4,525,157 | A * | 6/1985 | Vaillancourt | A61M 25/0111 | 604/165.01 |
| 4,850,960 | A * | 7/1989 | Grayzel | A61M 25/065 | 604/528 |
| 4,894,052 | A * | 1/1990 | Crawford | A61M 25/0693 | 604/507 |
| 5,100,390 | A * | 3/1992 | Lubeck | A61B 17/3401 | 604/274 |
| 5,474,534 | A * | 12/1995 | Schlitt | A61M 25/02 | 604/164.11 |
| 5,515,871 | A * | 5/1996 | Bittner | B23K 26/354 | 604/274 |
| 5,649,911 | A * | 7/1997 | Trerotola | A61M 25/0606 | 604/164.01 |
| 5,688,249 | A * | 11/1997 | Chang | A61M 25/0625 | 604/164.01 |
| 6,273,877 | B1 * | 8/2001 | West | A61B 17/3401 | 604/264 |
| 6,524,277 | B1 * | 2/2003 | Chang | A61M 25/0643 | 604/170.01 |
| 6,554,809 | B2 * | 4/2003 | Aves | A61B 17/3401 | 604/272 |
| 6,702,790 | B1 * | 3/2004 | Ross | A61M 5/3286 | 604/239 |
| 8,439,877 | B2 * | 5/2013 | Burkholz | A61M 5/329 | 604/110 |
| 8,603,037 | B1 * | 12/2013 | Wiley | A61M 25/0693 | 604/165.02 |
| 9,597,461 | B2 * | 3/2017 | Aasmul | A61M 5/3286 | |
| 2006/0276759 | A1 * | 12/2006 | Kinast | A61M 5/3286 | 29/2.25 |
| 2010/0016786 | A1 | 1/2010 | Drews et al. | | |
| 2010/0137804 | A1 * | 6/2010 | Wiley | A61M 5/3286 | 604/168.01 |
| 2011/0208215 | A1 | 8/2011 | Modesitt et al. | | |
| 2011/0295152 | A1 * | 12/2011 | Sasaki | A61B 5/150748 | 600/573 |
| 2014/0107569 | A1 | 4/2014 | Fischer et al. | | |
| 2015/0151084 | A1 | 6/2015 | Teoh | | |
| 2015/0151088 | A1 | 6/2015 | Lim | | |
| 2015/0305769 | A1 * | 10/2015 | Ibragimov | A61M 25/0606 | 606/180 |
| 2016/0045715 | A1 * | 2/2016 | Galgano | A61M 25/0662 | 604/510 |
| 2018/0093074 | A1 * | 4/2018 | Burkholz | A61M 25/0068 | |

FOREIGN PATENT DOCUMENTS

| | | | | |
|---|---|---|---|---|
| JP | 2011-250999 | A | 12/2011 | |
| WO | WO-9204062 | A1 * | 3/1992 | A61M 5/3286 |
| WO | WO 02/002161 | A1 | 1/2002 | |
| WO | 2016/187063 | A1 | 11/2016 | |
| WO | WO-2017017934 | A1 | 2/2017 | |
| WO | 2017/074684 | A1 | 5/2017 | |

OTHER PUBLICATIONS

Extended European Search Report dated Apr. 7, 2021, which issued in the corresponding European Patent Application No. 18840142.6.

* cited by examiner

METHOD AND APPARATUS FOR INTRODUCING A NEEDLE FOR CATHETER PLACEMENT

This application claims the priority to U.S. Provisional Application Ser. No. 62/541,158, filed on Aug. 4, 2017, which is hereby incorporated by reference in its entirety.

BACKGROUND OF THE INVITATION

Field of the Invention

The invention is in the field of needles, catheter insertion devices, and a method of introducing the needles into a patient where the needles have a tip with a shape and configuration to assist in the insertion into a vein or artery with a reduced incidence of transfixing the vein or artery caused by passing through or damaging the inner surface of the vein or artery. The invention is also directed to a method of introducing a needle into a patient with an improved ease of insertion and positioning of a catheter device in a vein for delivering a medication or drug to a patient. In one embodiment, the invention is directed to a catheter insertion device that can be operated in a manner to improve the efficiency of catheter insertion into a patient while reducing and minimizing the need for repeated attempts for proper placement of the introducer needle and catheter.

Description of the Related Art

Catheters are generally used for parenteral nutrition, IV fluid replacement and for administering analgesics and antibiotics. Catheters can be inserted at the bedside using sterile techniques and can remain in place for several weeks. The insertion (venipuncture) is performed above and below the antecubital fossa in the cephalic, basilic, or brachial veins. The catheter tip can be introduced into the vein and advanced the full length of the catheter.

Inserting and properly positioning an IV catheter on the first attempt generally requires a level of skill that that is not possessed by some clinicians. The accurate placement of a catheter and the insertion device in the vein on the first attempt is a great advantage to reduce the incidence of damage to the vein and/or the surrounding tissue. Proper placement of the catheter and the insertion needle is important to minimize the discomfort and pain to the patient as well as reducing damage or injury to the vein. Damage caused to the vein during insertion and placement of the catheter can cause accelerated clotting and thrombosis.

Some advantages of certain catheters are the reduced frequency of repeated venipunctures for labs/restarts, decreased incidence of catheter related infections, extended implant/indwell duration, improved clinical outcomes, patient satisfaction and associated cost savings. Placing the catheter tip in the larger diameter veins in the upper arm compared to the smaller veins provide improves drug delivery therapy and hemodilution. Catheters can be used for infusing contract media at higher flow rates that are typically done by CV catheters such as PICC applications.

Certain prior catheter devices can include an integral guidewire that is advanced through the lumen of a needle and into the vein after the needle accesses the vein. Often an ultrasonic probe or imaging device is used to locate the needle in the desired location. The catheter is then advanced over the guidewire into the vein. The needle and guidewire are then detached and separated from the catheter which remains in place in the vein.

The insertion needle or other insertion device typically requires a sharp tip to pierce the skin and the vein of the patient with minimal resistance to minimize the pain to the patient. The insertion needle is generally placed at a steep inclined angle with respect to the surface of the skin and the longitudinal dimension of the vein to be pierced to allow penetration through the skin and the wall of the vein. After the tip of the insertion needle pierces the wall the vein, the angle of the insertion is lowered to be able to slide the needle and catheter into the vein a distance sufficient to properly position the catheter in the vein. The initial steep angle of insertion can result in the sharp tip of the needle or insertion device piercing or damaging the inner surface of the wall of the vein at a location opposite the point of entry.

While the prior devices are generally suitable for the intended use, there is a continuing need for improved devices and method for introducing the devices for controlling the penetration of a needle or cannula for delivering a drug or medicament. In particular there is a need for an insertion device that is able to effectively pierce the skin and the vein while reducing the risk of injury or damage to the vein.

SUMMARY OF THE INVENTION

The present invention is directed to a needle and a method for the insertion of a needle, guide wire and/or catheter and a device for placement of an IV catheter in a selected location in the patient with reduced risk of transfixing the introducer needle through the wall of the vein. The invention is particularly directed to a method of orienting a needle for a catheter at a selected position and angle relative to the surface of the skin and inserting and placement of the catheter or guide wire in the vein or artery of the patient. The needle is able to place the catheter or guide wire in a selected location with reduced risk of damaging, transfixing, or injuring the vein during the process. The needle can be used with a guide wire for inserting the guide wire into the patient for advancing a catheter such an a IV catheter or PICC catheter.

A feature of the invention is to provide a method of introducing a needle into a vein of a patient where the needle has a configuration and orientation that is effective in piercing the skin and the vein during the insertion of a catheter and to reduce or minimize the risk of piercing or damaging the inner surface of the vein caused by transfixing. The needle of the invention is configured and oriented to assist in positioning the needle at an angle with respect to the surface of the skin and the longitudinal dimension of the vein during the insertion into the vein to reduce the risk of damaging the inner surface of the vein that can otherwise be caused by the sharp tip of the needle.

One feature of the invention is to provide a needle having a distal end with a sharp tip having a configuration for penetrating the skin and vein or artery while reducing the occurrence of damage or injury to the vein or artery during insertion. The needle can be a cannula for introducing fluids to the patient or can be used as an insertion needle for a catheter. The needle can be a solid needle or can include a lumen. In the embodiment where the needle is an insertion needle for a catheter or guide wire, the needle can include an opening or groove to provide flashback of blood when the needle penetrates the vein or artery.

The method of the invention introduces a needle into a vein where the needle includes a distal tip with a sharp point for penetrating the skin and penetrating the vein or artery of a patient and introducing at an orientation to minimize the risk of the sharp point from transfixing, penetrating, or injuring the inner surface of the vein or artery during penetration. The needle has a configuration so that the trajectory of the needle will promote a flattening of the angle of the needle after insertion to a lower angle with respect to the longitudinal direction of the vein or artery.

A method is also provided for introducing a catheter insertion device having a distal tip with a configuration that is able to penetrate the skin and vein or artery with minimal discomfort to the patient and effectively position a catheter in the vein or artery. The distal tip is able to easily penetrate the vein or artery at a suitable angle where contact of the distal tip is avoided with the inner surface of the vein or artery at a location opposite the point of penetration by the sharp tip.

The needle in one embodiment includes a body having a longitudinal dimension with a proximal end and a distal end. The body in one embodiment can have a substantially cylindrical shape that can be solid or hollow to define a lumen or passage through the needle. The body has a first longitudinal side surface and a second longitudinal side surface opposite the first longitudinal side surface. The second longitudinal side surface has a bevel surface converging toward the distal tip. In one embodiment, the needle is oriented at an inclined angle with respect to the surface of the skin of the patient where the bevel surface faces the surface of the skin of the patient and is introduced into the patient at an angle where the bevel surface promotes a substantially forward movement of the needle with respect to the longitudinal dimension of the vein.

In one embodiment, the insertion needle of the invention includes a distal tip configured to penetrate the vein or artery where the distal tip has a curved surface oriented to face the opposing wall of the vein opposite the point of penetration. The needle is inserted into the patient with the curved surface oriented so that contact of the curved surface with the inner surface of the vein or artery occurs rather than the sharp distal tip to reduce the damage or penetration to the inner surface of the vein or artery during insertion. The curved surface promotes the flattening of the angle of the needle to assist in inserting the needle in a direction substantially parallel to the longitudinal dimension of the vein or artery.

The various aspects and features of the invention are attained by providing a method of introducing a needle, such as an insertion needle, into a patient where a distal end of the needle has an inclined or bevel surface that converges toward a distal tip. The needle is inserted into the patient with the bevel surface facing the surface of the skin of the patient so that upon insertion into the vein, the bevel surface faces the wall of the vein at a location opposite the point of entry of the needle so that contact of the bevel surface with the inner surface of the vein reduces the transfixing or damage to the vein during the insertion by the distal tip of the needle.

The features of the invention are further provided by a method of introducing a catheter into the vein of a patient where the introducer needle has a body with a longitudinal dimension with a proximal end and a distal end, a first longitudinal side and a second longitudinal side opposite the first longitudinal side. The second longitudinal side has a distal end with a bevel surface that converges to a distal tip. A catheter is positioned on the introducer needle for insertion into the vein. The introducer needle and catheter pierce the skin and the vein at a first inclined angle with respect to the longitudinal dimension of the vein where the bevel surface faces the skin and vein during insertion. The distal tip of the needle is introduced into the vein with the bevel surface facing the inner surface of the vein at a location opposite a point of entry so that the distal tip does not contact the inner surface of the vein and the distal end of the catheter is positioned within the lumen of the vein. The catheter is then advance forward over the distal tip of the needle and positioned in the vein. In other embodiments, a guide wire can be advanced through the lumen of the needle.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which.

DETAILED DESCRIPTION OF THE EMBODIMENTS

A needle, such as a catheter insertion needle or guide wire, is provided for positioning a catheter in a patient for delivering a medication or other substance to a patient. The terms “needle” and “cannula” can be used herein interchangeably to refer to a member that can have a sharpened or beveled end for insertion into an injection site on a subject. In one embodiment, the needle can be a thin hollow tubular member. In other embodiments, the needle can be a solid member. As used herein, the “distal” direction is in the direction toward the patient and injection site, and the “proximal” direction is the opposite direction. “Axial” means along or parallel to the longitudinal axis of the needle or other member and the “radial” direction is a direction perpendicular to the axial direction.

The invention is directed to a method and apparatus for introducing a needle, a cannula or guide wire into a patient that can be used alone for introducing a substance to a patient or can be used with a catheter for inserting and positioning the catheter into the vein or artery of a patient. In the illustrated embodiments, the needle is used with a catheter for positioning the catheter in the vein of the patient although the needle is not limited to use with a catheter. The needle can include a lumen for delivering a substance and providing flashback when the vein or artery is pierced. In other embodiments the needle can be a solid body with or without a flashback feature. In further embodiments, the device can be used with a guide wire for introducing a catheter into a patient. In the following description, the needle refers generally to a hollow or solid member suitable for positioning a catheter or guide wire in a selected location in a patient.

Figure 1:
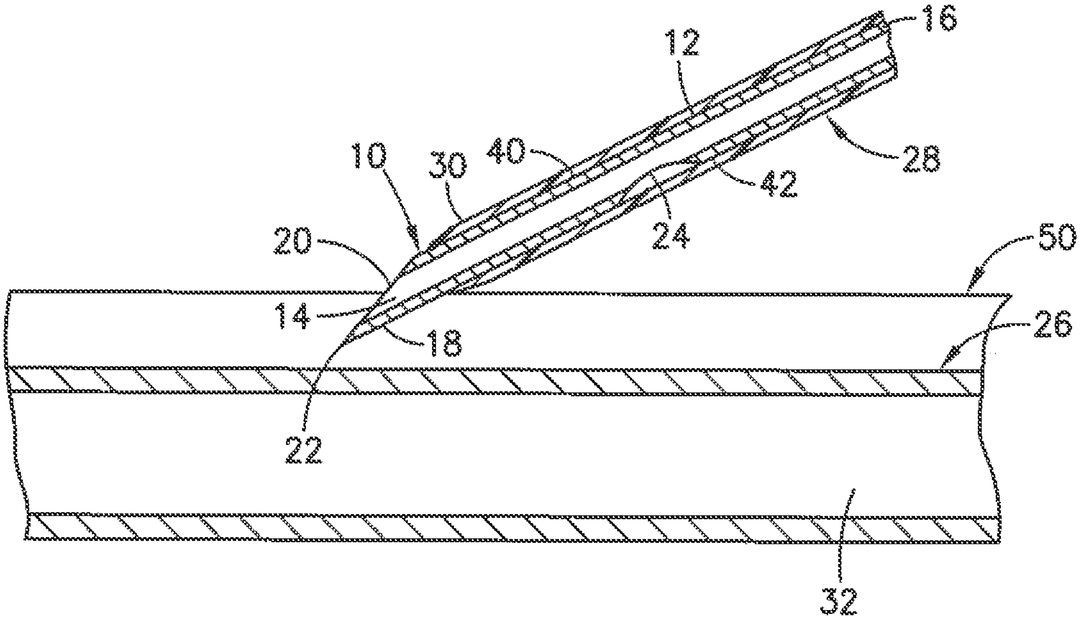
FIG. 1 is a side perspective view of a standard needle and catheter showing the needle piercing the skin of the patient with the bevel surface facing away from the patient.
Figure 2:
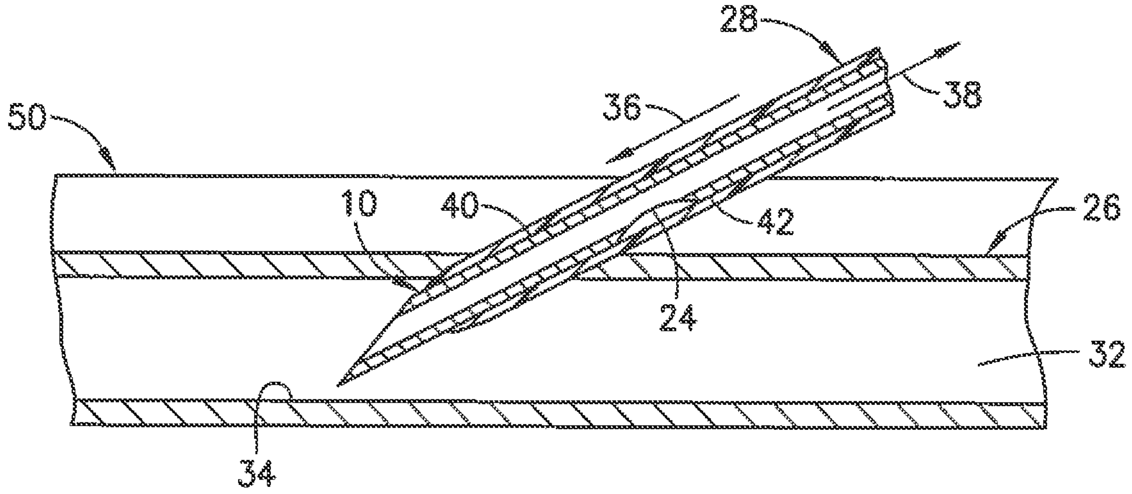
FIG. 2 is a side view of the needle of FIG. 1 penetrating the vein and the distal end of the catheter partially positioned in the vein during the insertion step.

Referring to the drawings, a needle 10 as shown in FIG. 1 and FIG. 2 has a needle body 12 with a first longitudinal side surface 40 and a second longitudinal side surface 42, and a lumen 14 extending between a proximal end 16 and distal end 18. A bevel 20 is formed to provide a major surface at an inclined angle relative to the longitudinal dimension of the body 12 and extends from an outer edge of the body at a distal end of the first longitudinal side surface 40 of the needle body 12 across the diameter of the needle body 12 to a second longitudinal side surface 42 of the needle body. In the embodiment shown, a single bevel surface 20 is formed that converges to a sharp distal tip 22 and where the bevel surface 20 faces outward from the first longitudinal side surface 40. The bevel 20 can be formed at an inclined angle of about 12-22° and typically about 15-17° with respect to the longitudinal axis of the needle. The sharp distal tip 22 is formed at the second longitudinal side surface 42 in the embodiment shown. Bevel surface 20 can be substantially flat as shown, convex, or concave. In alternative embodiments, a second reverse bevel and a third reverse bevel can be formed opposite the bevel 20. The reverse bevels can be formed at an incline to each other and converge with the bevel 20 to form the sham distal tip. A notch 24 or other opening for providing blood flashback is provide in the wall of the needle body on a side opposite the bevel surface 20 to provide improved visibility of the flashback during insertion when the bevel surface 20 faces the surface of the skin and vein.

Figure 9:
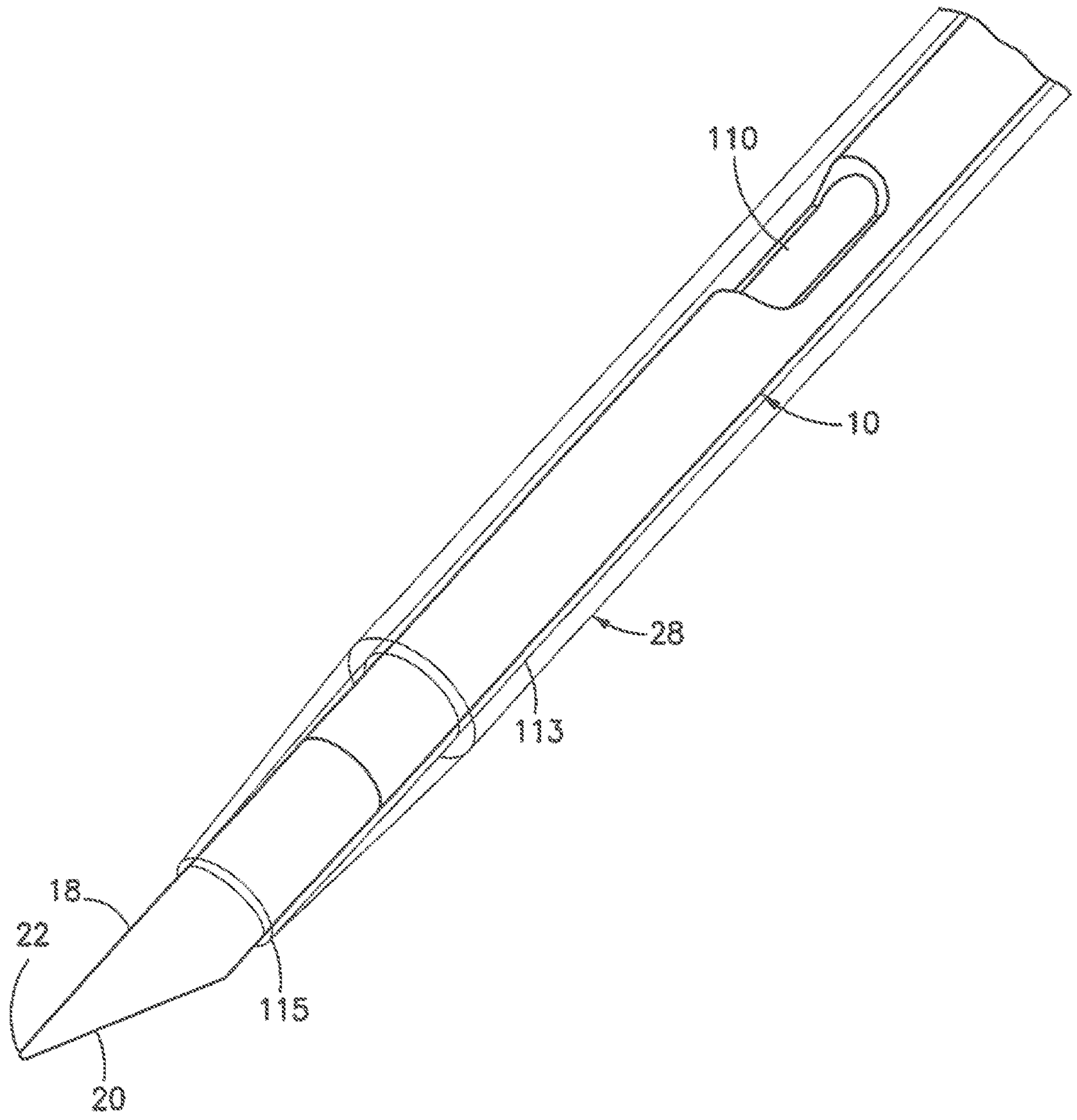
FIG. 9 is a perspective view of the needle and catheter showing the flashback notch in the needle.
Figure 10:
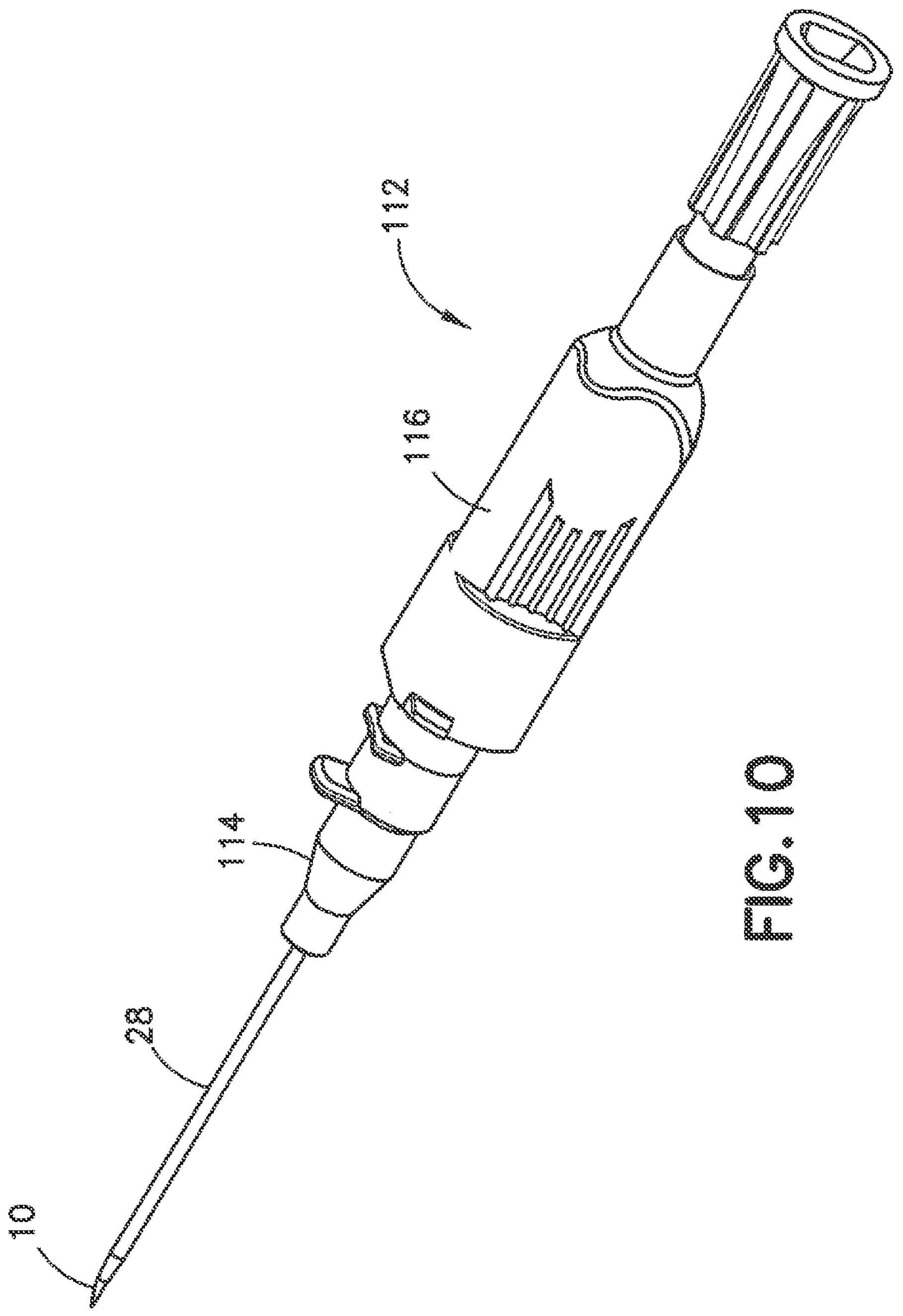
FIG. 10 is a perspective view of the catheter assembly for introducing the catheter into the patient.
Figure 11:
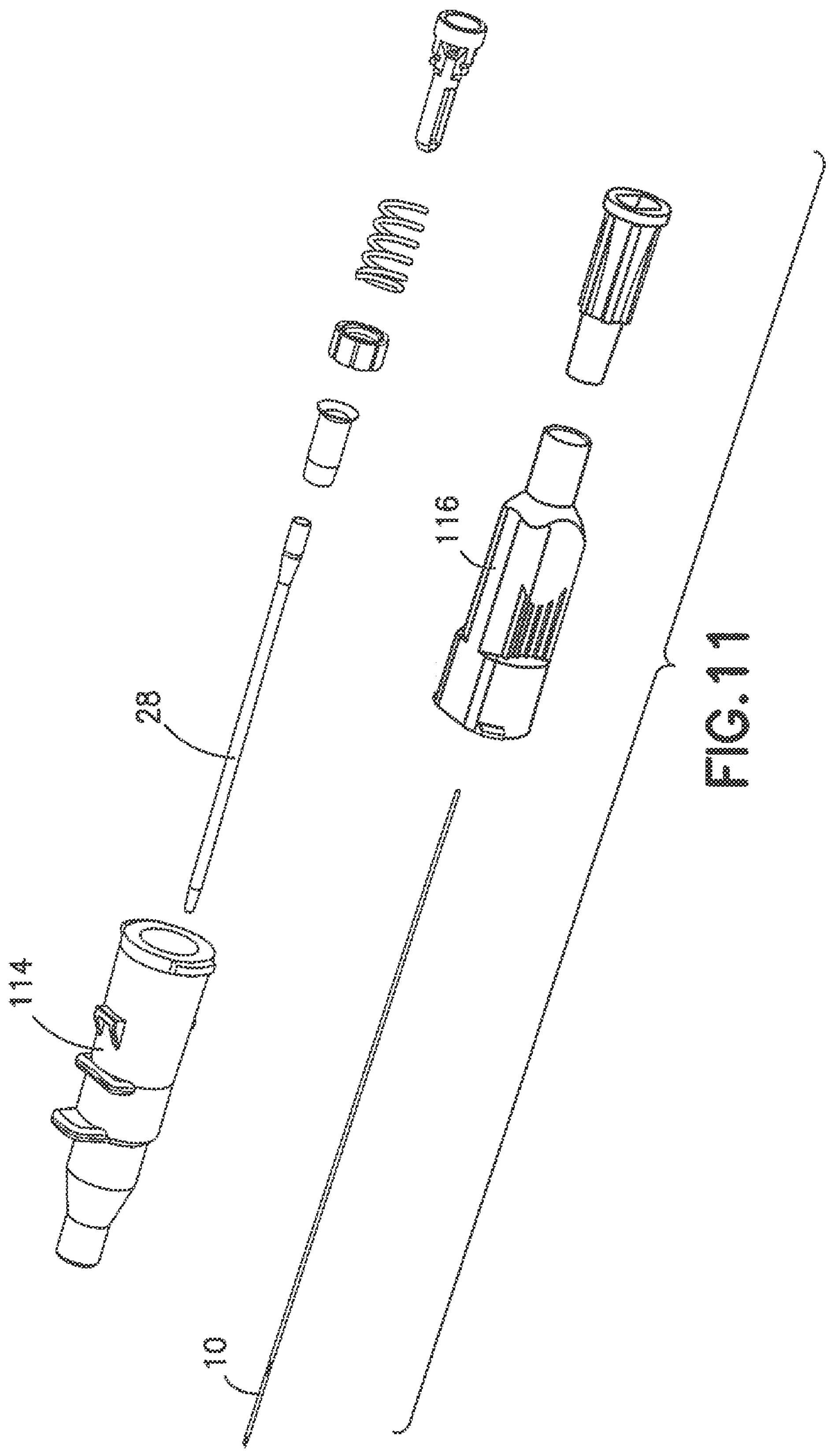
FIG. 11 is an exploded view of the catheter assembly of FIG. 10.
Figure 12:
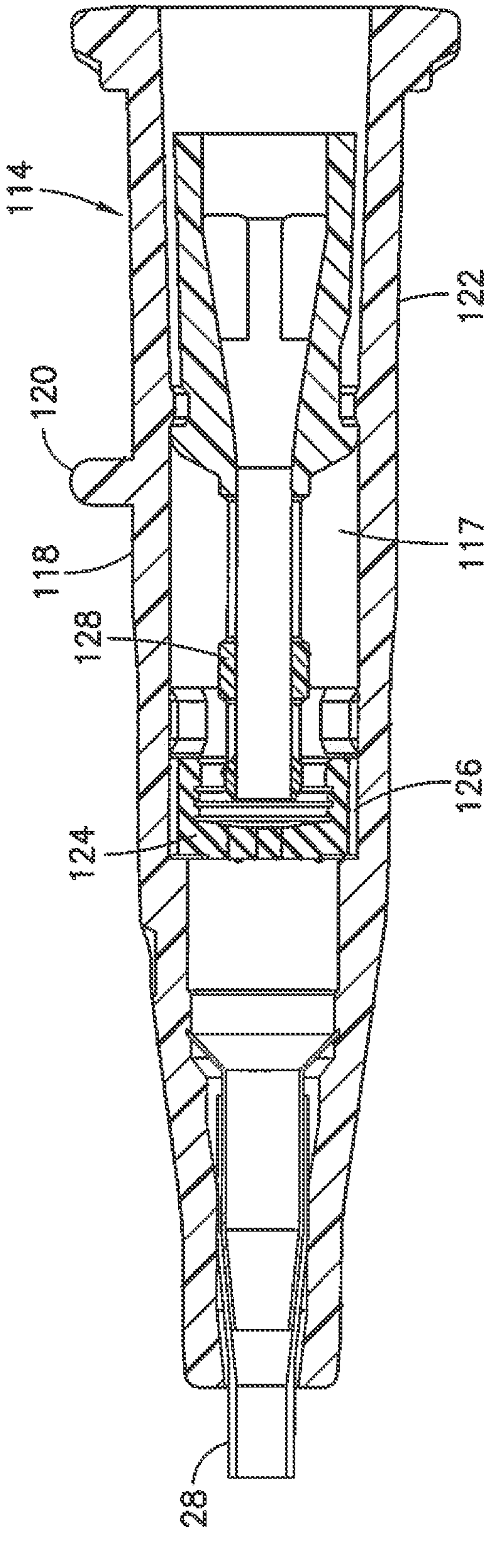
FIG. 12 is a partial cross sectional view of the catheter assembly.

The needle 10 is generally used with a catheter assembly 112 and includes a blood flashback feature to provide an indication that the distal end of the needle is positioned in the vein. The flashback feature in FIG. 9 is shown as the lumen extending from bevel surface 20 through needle 10 to a location and/or device where the blood can be visualized between the needle and catheter by the clinician during insertion of the needle and catheter. The flashback feature can be a notch forming an opening 110 in the side wall of the needle shown in FIG. 9 to allow blood to exit the needle and pass between the catheter 28 and the needle where blood can be visualized by the clinician to provide an indication that distal tip 22 of the needle has entered the lumen 32 of vein 26. The catheter is configured so that the distal end of the catheter is constricted at the end 115 around the distal end of the needle and a gap or passage 113 is formed proximally of the constricted end to receive the blood passing through the notch where the blood is visible to the clinician. In the embodiment shown, the notch 110 is formed on a longitudinal side of the needle opposite the bevel surface 20 to improve the visibility of the flash back when the bevel of the needle is oriented to face the surface of the skin of the patient during insertion and placement of the catheter.

Catheter assembly 112, as shown in FIGS. 10-13, includes the needle 10 functioning as an introducer needle, a catheter hub 114, and a needle hub 116. The needle 10 can have a sharpened distal end 18 that extends through the catheter hub 114. An example of a catheter hub assembly having a blood flashback feature is disclosed in WO2015/161294, which is hereby incorporated by reference in its entirety. The flexible catheter 28 extends from the distal end of the catheter hub 114, with the needle 10 passing through the catheter 28. Initially, the needle 10 is inserted into a patient's vein. The catheter 28 is pushed along the needle 10 by tabs on the catheter hub and into the vein following the needle 10. After inserting the catheter 28, the needle 10 is removed from the patient's vein and the catheter hub 114, leaving the catheter 28 in the patient. The needle 10 is discarded after withdrawing from the catheter.

Catheter hub 114 has a distal end, a proximal end, and an outer surface. The distal end includes a catheter opening and the proximal end includes a Luer connector opening with projections for coupling with the Luer connector. A channel 117 shown in FIG. 12 permits fluid passage through the catheter hub 114. The outer surface on a first longitudinal side surface 118 of catheter hub 114 includes one or more projections 120, such as thumb or finger tabs, for manually manipulating the catheter hub 114 during insertion into the patient. The projections can be a thumb tab to assist the clinician in holding and manipulating the catheter assembly 112 during use. A second longitudinal side surface 122 opposite the first longitudinal side surface 118 in the embodiment shown is substantially flat to lie easily against the skin of the patient during use without interference from projections, tabs or the like. The catheter hub 114 may be made from a polymer material that is transparent or semi-transparent so that fluid flow through the catheter hub may be observed by a user or it may be made from an opaque material. In the embodiment shown, needle 10 is oriented where the first longitudinal side surface 40 of needle 10 faces outwardly from the second longitudinal side surface 122 of catheter hub 112 so that the flat bevel 20 faces outwardly from the second longitudinal side surface 122 of catheter hub 112 during use. The sharpened distal tip 22 is aligned with the first longitudinal side surface 118 and projections 120 of catheter hub 112.

The flexible catheter 28 extends through the catheter opening and is secured to the catheter hub 114. A pre-slit resilient septum 124 is positioned in the channel to form a fluid-tight seal and selectively admits fluid to or from the flexible catheter 28. The septum selectively permits or blocks the flow of fluid through the flexible catheter 28.

The septum 124 includes a plurality of axial flow channels 126 on an outer circumference of the septum 124. The flow channels 126 have an appropriate width and depth so that when the septum 124 is not opened, blood can enter and air can escape the space distal of the septum 124 in the front portion of the catheter hub. At the same time, the flow channels 126 are sized small enough to prevent the blood from exiting past the septum for a period of time. When the catheter 28 is initially inserted into a patient, and the introducer needle 10 is removed, the septum 124 prevents blood from flowing through the channel and out of the distal end. The septum 124 is made of an elastic material, for example silicone rubber. Other elastic materials may be used and non-elastic materials may be incorporated in the septum 124 as needed.

An actuator 128 is positioned in the channel and is axially moveable in the channel to engage and open the slits of the septum 124. The actuator is a substantially tubular member and with an internal passage to allow fluid to flow through the actuator 128 and through the septum 124 when the septum 124 is opened or penetrated by the actuator 128.

Figure 13:
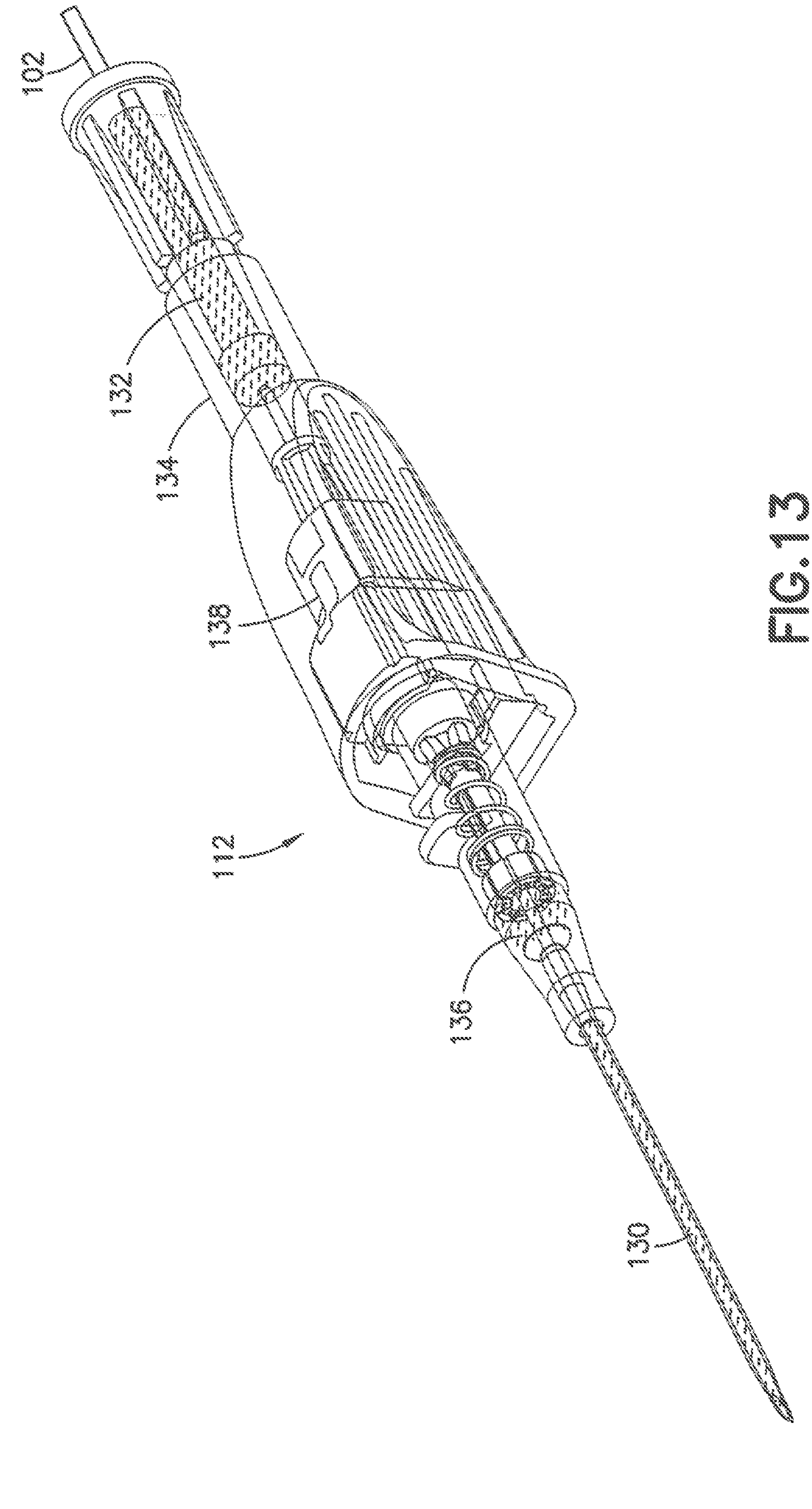
FIG. 13 is perspective view of the catheter assembly showing the flashback features.

FIG. 13 illustrates an exemplary embodiment of blood flashback features in the catheter assembly 112. Flashback is the visibility of blood that confirms the entry of the needle tip into the vein. Primary flashback indicated by reference number 130 shown in FIG. 13 is seen through the catheter 28 as blood travels into the open distal end of the hollow needle 10, out a notch or opening in the needle 10 near the needle tip, and up through the internal annular space between the needle 10 and the inside of the catheter 28. The secondary flashback 132 is seen in the needle hub/grip 134 forming a blood control member when blood comes out of the back of the needle 10 and enters a flash chamber in the needle hub/grip 134. Air is vented by the plug in the back of the needle hub/grip 134 by a porous membrane or micro grooves. Tertiary flashback 136 is visible in the catheter hub 114 when the blood from the primary flashback flows into the catheter hub and stops at the blood control septum. A safety mechanism 138 shown in FIG. 13, such a spring clip or other blocking member is provided to capture the end of the needle to prevent accidental needle stick and re-use of the needle. An example of a safety mechanism and needle protection member is disclosed in US 2017/0043134, which is hereby incorporated by reference in entirety.

In the embodiment shown, catheter 28 is positioned on needle body 12 in a catheter assembly 112 with a distal end 30 of catheter 28 positioned at the distal end of needle body 12. The distal end of needle body 12 extends from the catheter a distance to enable the needle to pierce the vein and enable the catheter to be positioned in the lumen of vein. A guide wire 102 as shown in FIG. 13 can be used with the assembly 112 to pass through the needle during the placement of the catheter in the vein of the patient.

Figure 3:
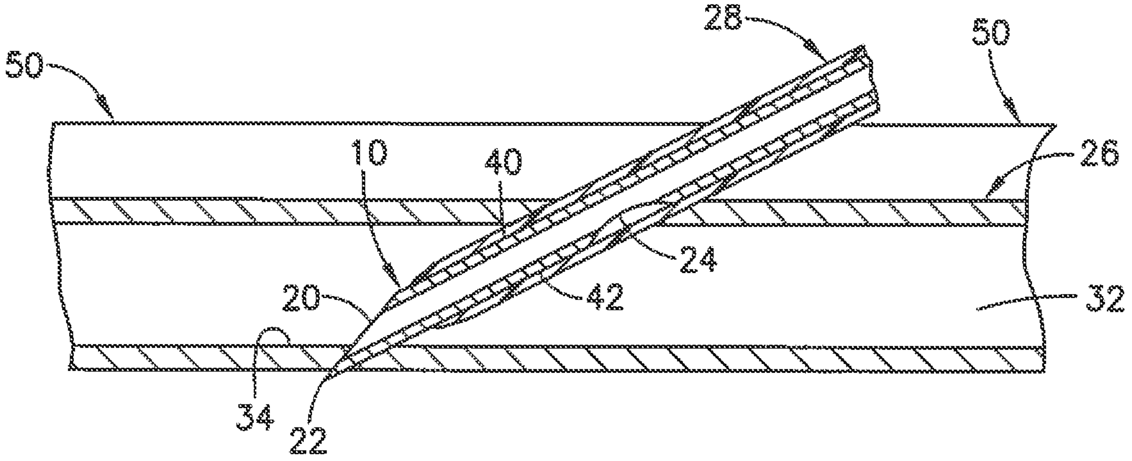
FIG. 3 is a side view showing the sharp distal tip of the needle piercing the inner surface of the vein.

FIGS. 1-3 show a method of insertion of needle 10 and catheter 28 into vein 26 of the patient where bevel 20 of needle 10 is oriented to face away from the patient in a generally upward direction with respect to the surface of the skin indicated generally by reference number 50. As shown in FIG. 1, needle 12 and catheter 28 are positioned at a first inclined angle relative the surface of the skin and the longitudinal dimension of vein 26 or artery with shamed distal tip 22 pointed toward the vein and the bevel surface 20 facing away from the vein in the upward direction away from the surface of the skin 50. Needle 10 is advanced in a substantially linear direction to pierce vein 26 at the first inclined angle with respect to a longitudinal dimension of the vein 26 as shown in FIG. 2 where distal tip 22 is positioned in lumen 32 of vein 26. As shown is FIG. 2, when distal tip 22 is positioned in lumen 32 and bevel surface 20 faces away from the inner surface on the for side 34 of vein 26, distal tip 22 contacts the surface of the vein at the far side 34 of vein 26 before distal end 30 of catheter 28 is completely received in lumen 32 of vein 26.

The needle 10 and catheter 28 in the position shown in FIG. 2 when provided with a flashback feature provide an inaccurate indication of proper positioning of needle 10 and catheter 28 in vein 26 where catheter 28 cannot slide easily from the end of needle 10. As shown in FIG. 2, distal tip 22 can contact the far side 34 of vein 26 that can damage vein 26 and cause trauma or thrombosis. In addition, the upper portion of the distal end of the catheter 28 is not positioned in the lumen 32 of vein 26 so that attempts in sliding catheter 28 from needle 10 will be hindered by the distal end of catheter 28 directly contacting the outer surface of the wall of vein 26 at the insertion and penetration site. The interference of catheter 28 with the outer surface of the wall of vein 26 can cause kinking and/or difficultly in sliding catheter 28 from the needle 10 into the lumen 32 of vein 26 as well as discomfort to the patient. In the embodiment shown, the blood flashback feature is provided by the lumen 14 of needle 10 that can carry an amount of blood to a point where the blood can be visualized before the distal end of catheter 28 is completely received in the lumen 32 of vein 26. The premature flashback before the entire end of the catheter is positioned in the vein or artery provides the clinician with an inaccurate indication of the catheter position in the vein. The premature flashback gives a false indication that the catheter is positioned in the lumen of vein 26 where catheter 28 can be properly advanced into the lumen of vein 26.

As shown in FIG. 3, further advancing of needle 10 and catheter 28 can result in distal tip 22 piercing or damaging the inner surface of the vein 26 at the far side 34 of vein 26 opposite the penetration site. Catheter 28 is forced against the inner surface of vein 26 to properly position distal end 30 of catheter 28 in vein 26 where distal end 34 is completely positioned within vein 26. In the position shown in FIG. 3, catheter 28 does not easily slide from the end of needle 10 and applies a force against the wall at the far side 34 of the inner surface of vein 26 opposite the penetration site. In addition, the angle of the needle requires the catheter to bend around sharp distal tip 22 where sharp distal tip 22 can cause skiving and damage to the inner surface of catheter 28 and/or can interfere with the sliding movement of catheter 28 from needle 10 into the vein.

Figure 4:
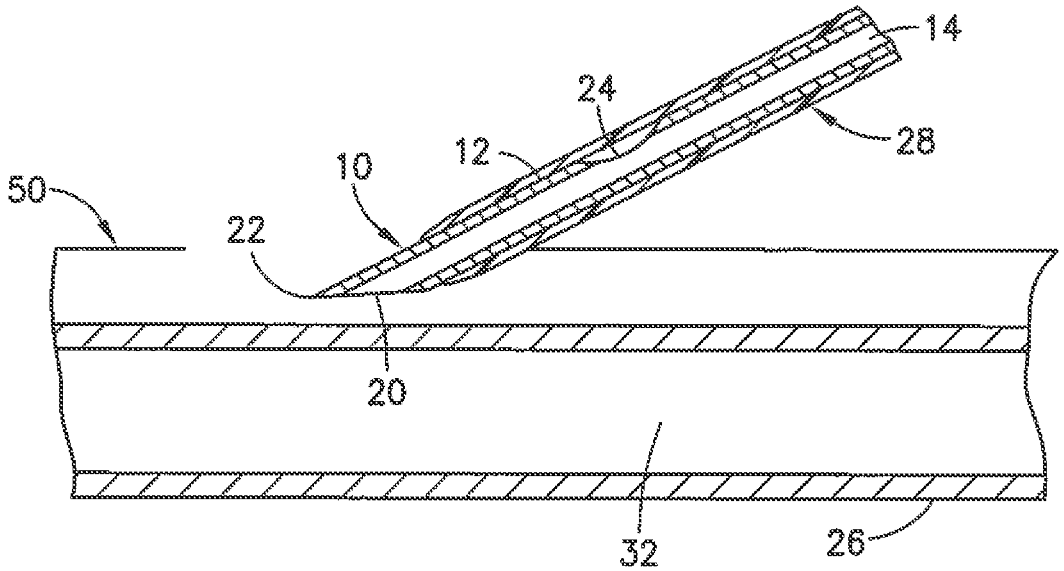
FIG. 4 is a side view showing the orientation of the needle and the angle of the needle prior to penetration of the needle into the patient in an embodiment of the invention.
Figure 5:
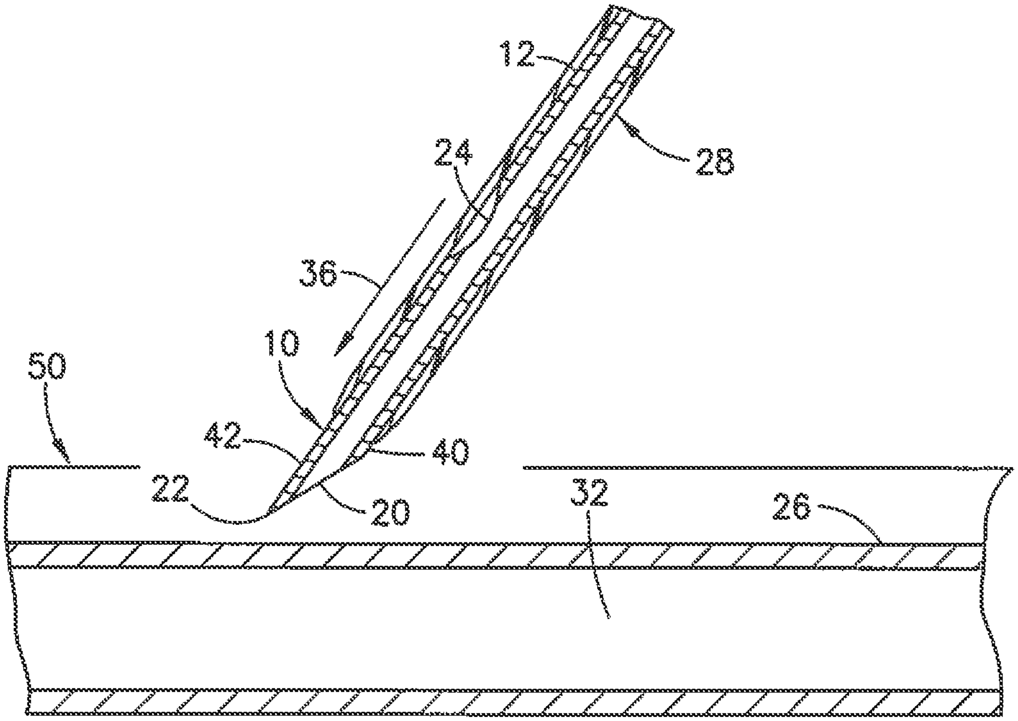
FIG. 5 is a side view showing the orientation and initial angle of penetration of the needle into the patient.
Figure 6:
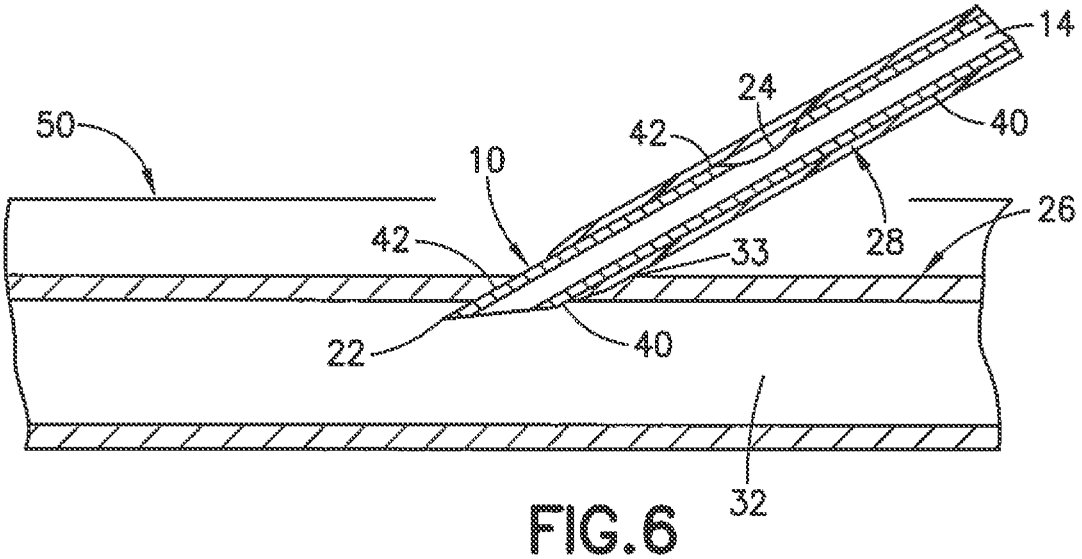
FIG. 6 is a side view showing the needle and catheter of the invention moving in a forward direction in the vein.
Figure 7:
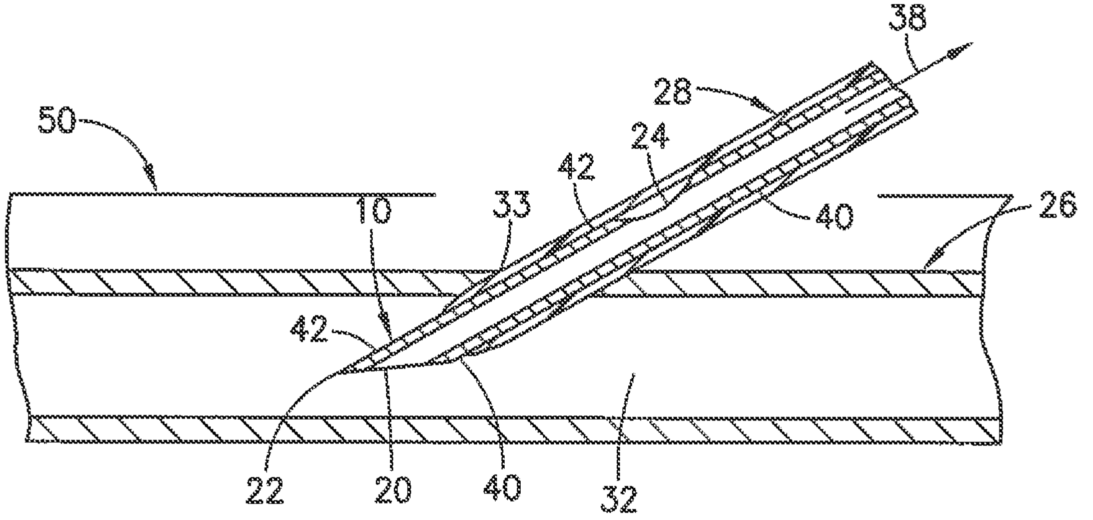
FIG. 7 is a side view of the needle and catheter positioned in the vein.
Figure 8:
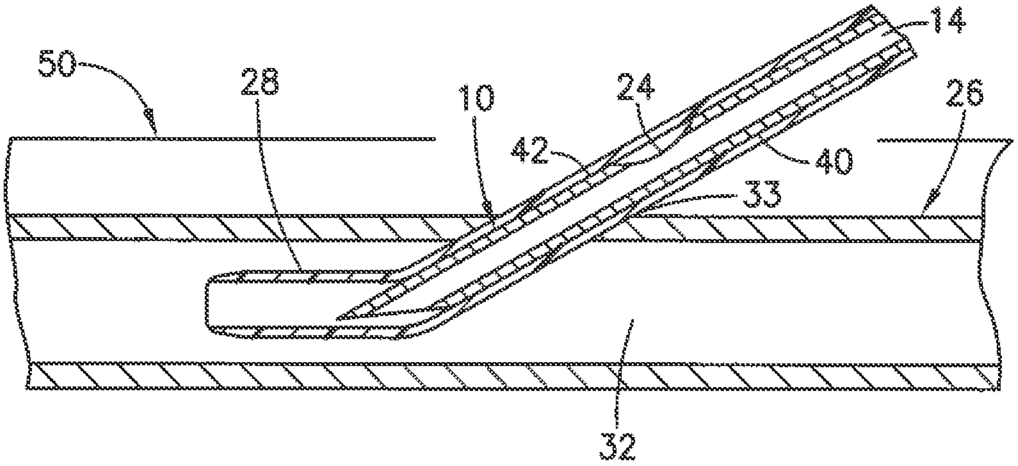
FIG. 8 is a side view of the needle of FIG. 7 showing the catheter advanced over the end of the needle.

FIGS. 4-8 illustrate one embodiment of the method for introducing the needle and catheter into the vein with increased reliability and reduced chances of transfixing the vein or obtaining a false flashback indication to reduce the risk of improper placement in the vein. As shown in FIG. 4, needle 10 and catheter 28 are oriented with respect to the surface of the skin and vein 26 with bevel 20 facing downwardly and toward the vein 26 and the surface of the skin 50, in one embodiment, the needle is 18 to 22 gauge and the bevel surface has a bevel angle of about 10 to 20°. In other embodiments, the needle can have a bevel angle of about 12° to 15°. Needle 10 is introduced into vein 26 by orienting in the position shown in FIG. 5 where the tip 22 at the distal end 18 contacts vein 26 and bevel 20 faces a top or outer surface of vein 26. An insertion force is applied in the direction of arrow 36 to needle 10 and catheter 28 to pierce the surface of the skin and the vein 26 as shown in FIG. 5 at a first inclined angle relative to the surface of the skin and the longitudinal dimension of the vein. In one embodiment, the insertion force is applied in a linear direction with respect to a longitudinal dimension of the needle. Bevel surface 20 is angled at an incline with respect to the longitudinal dimension of vein 26 to assist needle 10 to slide in a substantially forward longitudinal direction of the vein relative the insertion direction of the needle and catheter by the clinician. The insertion force and the bevel 20 promote the flattening of the angle of the needle by the bevel sliding in a substantially forward longitudinal direction through the slit or cut at a point of entry 33 formed in vein 26 as shown in FIGS. 6 and 7. In the embodiment show, the orientation of the bevel surface with respect to the outer surface of the vein and the surface of the skin at the initial penetration is at an inclined angle by the longitudinal axis of the needle oriented at an incline of about 55 to 65°, and typically about 60° with respect to the surface of the skin to provide piercing of the skin and the vein. As the tip 22 pierces the vein as shown in FIG. 6, the bevel angel promotes a change in the incline angle of the needle and bevel surface with respect to the longitudinal dimension of the vein. After penetration of the vein, the angle of the needle is reduces to about 25° to 35' and typically about 30° with respect to the longitudinal dimension of the vein.

Referring to FIG. 7, further advancement of needle 10 and catheter 28 enable needle 10 and catheter 28 to penetrate vein 26 so that bevel 20 and distal end 30 of catheter 28 are positioned completely in the lumen 32 of vein 26 with a reduced risk of the distal tip piercing or transfixing the vein at the far side from the point of entry. As shown in FIG. 7, distal tip 18 and bevel 20 are able to pierce the wall of vein 26 at the point of entry and be positioned completely within lumen 32 without distal tip 22 piercing far side 34 of vein 26 during the insertion step to reduce the occurrence and inhibit transfixing by the needle 10. The bevel 20 is able contact the inner surface of vein 26 with an effective placement of needle and the distal end of catheter 28 in lumen 32 while reducing the occurrence of injury to the inner surface of the vein. As shown in FIG. 7, the distal end of catheter 28 is completely within lumen 32 of vein 26 so that blood flashback through lumen 14 in needle 10 as indicated by arrow 38 provides an accurate indication that the distal end of the catheter 28 is properly positioned in lumen 32 of vein 26.

Once needle 10 and catheter 28 are positioned in lumen 32 of vein 26, catheter 28 can be advanced in a forward direction to slide the catheter from the needle into vein 26 with reduced resistance and interference compared to the prior method and orientation of the bevel surface of the needle with respect to the longitudinal dimension of the vein. The flexible catheter 28 is able to slide over bevel 20 with minimal resistance without sliding or bending over sharp distal tip 22 to avoid skiving or damage to catheter 28. In the embodiment shown, the proximal end of the bevel surface at the outer surface of the needle form an obtuse angle so that the inner surface of the catheter is able to slide over the intersection between the bevel surface and the outer surface of the needle without damaging the inner surface of the catheter. The bevel surface can be oriented at an angle where the tip 22 is at an angle relative to the longitudinal dimension of the vein to prevent or minimize damage or injury to the inner surface of the vein. Needle 10 can then be removed from catheter 28 in a usual manner.

Figure 14:
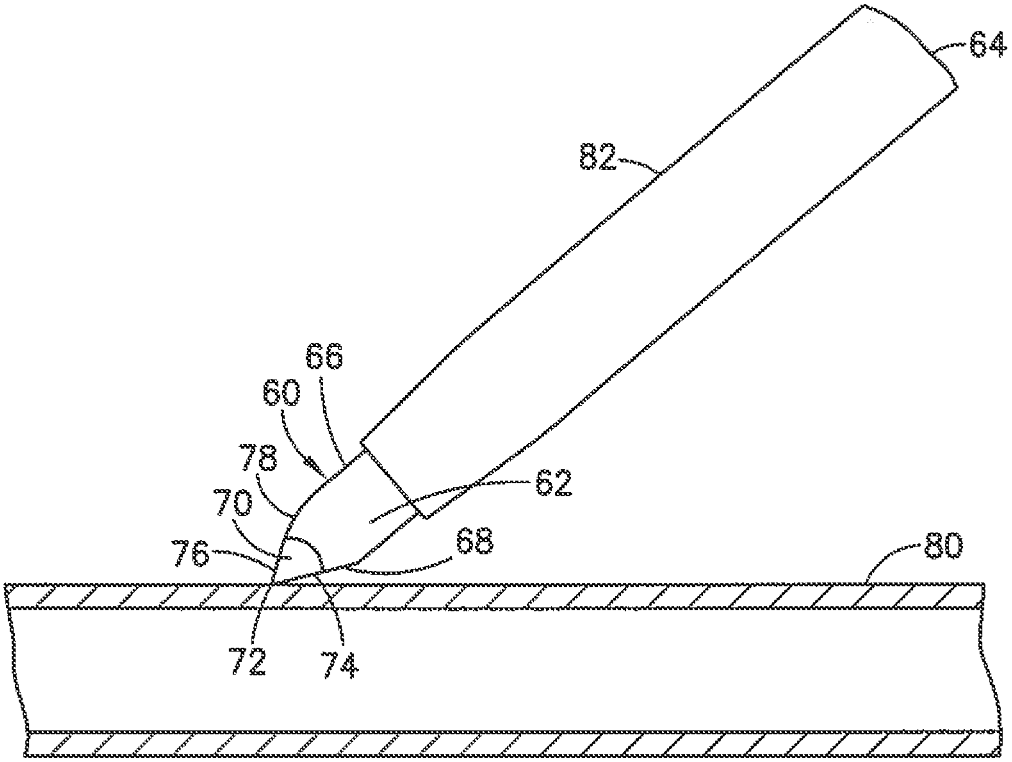
FIG. 14 is a side view of a needle in another embodiment showing the shape of the tip of the needle and orientation for inserting into the patient.
Figure 15:
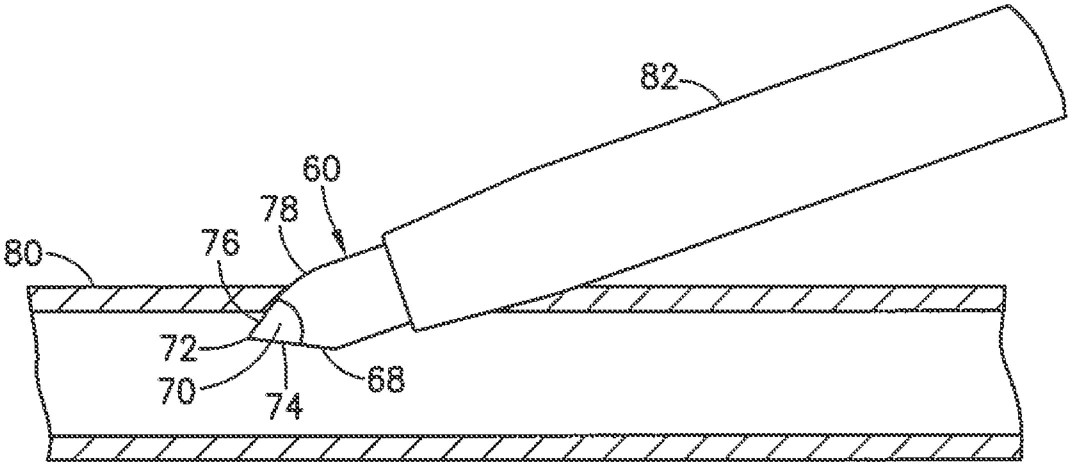
FIG. 15 is side view of the needle of FIG. 14 and the orientation of the needle during insertion into the patient.

In another embodiment shown in FIG. 14 and FIG. 15, the needle 60 has a longitudinal cylindrical body 62 with a proximal end and a distal end 66. The distal end 66 is formed with a first major bevel 68 cut at an angle of about 16-22° and two reverse bevels 70 on opposite sides to form a sharp tip 72 formed by three cutting edges between the respective bevels. The reverse bevels 70 converge with the first bevel 66 to form the tip 72. The bevels 70 converge with the first bevel 68 at an acute angle to form angled cutting edges 74 that extend from the tip 72. The cutting edges 74 are formed at an angle of about 75-85 with respect to one another. The reverse bevels 70 converge with each other to form an inclined cutting edge 76 extending from the tip 72 toward the outer surface of the needle body on a side opposite the bevel 66 and in a direction toward the proximal end of the needle body. A rounded curved distal end portion 78 extends from the outer peripheral surface of the body 62 to the cutting edge 76 so that the cutting edge 76 is spaced radially inward with respect to the outer peripheral surface of the body.

The needle 60 supports a catheter 82 in manner similar to the previous embodiment. The method of inserting the needle and catheter into the patient orients the needle 60 with the bevel 68 facing the surface of the skin of the patient and the vein 80. The needle is advance in a substantially linear direction into the vein with the cutting edges piercing the vein 80 until the curved surface 78 of the distal end portion contacts the wall of the vein 80 as shown in FIG. 15. The curved surface 78 contacts the vein and slides through the opening formed in the vein without further cutting. The curved surface spaced radially outward from the cutting edge promotes the sliding movement of the needle tip into the vein with reduced discomfort to the patient. The catheter 82 then slides over the end of the bevel 68 into the vein. In other embodiments a guide wire can be used in combination with the needle.

Other examples of a flashback feature include a substantially V-shaped groove or recess on an outer surface of the needle. In one embodiment the wall of the needle can be crimped to form a groove and a protruding portion extending into the axial passage of the needle. The protruding portion can form a surface to reduce the inner diameter of the needle to reduce the incidence of coring during insertion into the skin and vein of the patient.

In the embodiment shown and described, the needle is used in combination with a catheter for piercing the vein and positioning the catheter in the vein with the needle in a position or orientation to complement the insertion and positioning of the catheter in the vein with reduced transfixing and damage or injury to the vein that can cause clotting and/or thrombosis, in other embodiments, the needle can be used alone without a catheter for drawing blood or introducing a fluid into the patient. Alternatively, the needle can be a solid core with or without a groove or lumen for providing blood flashback.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A method of introducing a needle and catheter into a vein or artery of a patient comprising the steps of:

providing a catheter and a needle, said needle having a body with a proximal end and a distal end extending from a distal end of said catheter, a first longitudinal side surface and a second longitudinal side surface opposite said first longitudinal side surface, said distal end having a first bevel at an angle of about 16-22° extending between said first longitudinal side surface and second longitudinal side surface, a second reverse bevel, and a third reverse bevel converging to said distal tip at an angle of about 75-85° and forming a first cutting edge between the second reverse bevel and the third reverse bevel, and extending between said distal tip and a curved distal surface extending distally and inwardly from an outer peripheral surface of the needle such that the first cutting edge terminates inwardly and distally of the outer peripheral surface, the second and third reverse bevels forming cutting edges between said first bevel and said second reverse bevel, and between said first bevel and said third reverse bevel, wherein the curved distal surface extends from the outer peripheral surface to a proximal end of the first cutting edge, said method comprising piercing the vein or artery where the first cutting edge and curved distal surface face outwardly from a skin surface and contact a distal surface of an insertion site;

orienting said needle at a first angle that is greater than the angle of the first bevel, where said first bevel faces an outer surface of the vein or artery and the distal tip contacts an outer surface of the vein or artery at an angle to pierce the vein or artery before said first bevel contacts the vein or artery;

applying a substantially linear insertion force to said needle to pierce a wall of the vein or artery with the first cutting edge until the curved distal surface contacts the wall of the vein or artery, and then orienting the needle at a second inclined angle relative to a longitudinal dimension of the vein or artery that is less than said first angle and less than the angle of the first bevel, and introducing said needle into a lumen of the vein or artery with said first bevel surface facing an inner surface of said vein or artery in a location opposite the insertion site by said needle, wherein said second inclined angle is smaller than said first inclined angle, and said curved surface contacts the vein or artery and guides said needle into the vein or artery without further cutting the vein or artery.

2. The method of claim 1, wherein said second longitudinal side surface of said needle has a notch defining a blood flashback passage between said needle and said catheter, and where said notch is oriented on a side opposite said first bevel.

3. The method of claim 1, further comprising orienting said first bevel with respect to the longitudinal dimension of the vein or artery to promote angular movement from said first inclined angle to said second inclined angle during insertion.

4. The method of claim 1, further comprising inserting said distal tip into a lumen of the vein or artery in a position spaced from an inner wall surface of the vein or artery opposite the insertion site and pointing in a direction substantially parallel to the longitudinal dimension of the vein or artery.

5. The method of claim 1, wherein said catheter includes a catheter hub with a first side and a second side opposite said first side, and a push tab on a first side, orienting said catheter relative to said needle where said first bevel faces outwardly from said second side of said catheter hub, said method further comprising advancing said catheter over said needle whereby said distal tip and said first cutting edge do not contact an inner surface of said catheter.

6. A method of introducing a catheter into a vein or artery of a patient comprising the steps of:

positioning a catheter and needle at a first inclined angle with respect to a longitudinal dimension of the vein or artery, said catheter having a catheter hub with a first side having a push tab and a second side opposite said first side, said needle having a body with a proximal end, a distal end, a first longitudinal side surface and a second longitudinal side surface opposite said first longitudinal side surface, said distal end having a first bevel extending between said first longitudinal side surface and said second longitudinal side surface, a second reverse bevel and a third reverse bevel converging to a distal tip and forming a first cutting edge between the second reverse bevel and the third reverse bevel extending between said distal tip and a curved distal surface extending distally and inwardly from an outer peripheral surface of said needle, said distal tip and cutting edges spaced radially inward from the outer peripheral surface of said needle, said second longitudinal side having a notch defining a blood flashback passage between a lumen of said needle and said catheter, and where said notch is oriented opposite said first bevel, and a guide wire extending though said needle, and wherein the second reverse bevel and the third reverse bevel converge with said first bevel to form said first cutting edges between said first bevel and said second reverse bevel, and between said first bevel and said third reverse bevel, wherein said first cutting edge faces a direction opposite said first bevel and faces towards said second longitudinal side of said needle and outwardly from said second side of said catheter hub, and where said first cutting edge is spaced radially inward with respect to said outer peripheral surface; and wherein the first cutting edge terminates inwardly and distally of the outer peripheral surface, and the curved distal surface extends from the outer peripheral surface to a proximal end of the first cutting edge;

piercing the vein or artery at said first inclined angle where said distal tip penetrates and the first cutting edge cuts a surface of the vein or artery at said first inclined angle where said first bevel surface faces the vein or artery and said inwardly curved distal surface faces outward with respect to the vein or artery and outwardly from said first side of said catheter hub until the curved distal surface contacts the surface of the vein or artery; and then inserting said needle and catheter through an insertion site into a lumen of the vein or artery at a second angle where said first bevel faces an inner wall surface of the vein or artery at a location opposite a point of penetration of said needle and catheter and said curved distal surface passes through the insertion site without further cutting the vein or artery to promote orientation of said distal tip toward an axis of the lumen, and advancing said catheter over said needle where said distal tip does not contact an inner surface of said catheter;

wherein the first bevel is inclined relative to the first longitudinal surface at a first bevel angle, the first inclined angle is greater than the first bevel angle, and the second angle is less than the first bevel angle.

7. The method of claim 6, further comprising orienting said first bevel with respect to said longitudinal dimension of the vein or artery to promote angular movement from said first inclined angle to said second inclined angle during said insertion step.

8. The method of claim 6, further comprising orienting said first bevel toward an inner surface of said opposing wall surface of the vein or artery at a location opposite the point of entry of said needle into the vein or artery.

9. The method of claim 6, further comprising orienting said distal tip at an incline to space said first bevel from said inner surface of said inner wall of said vein or artery during insertion into the vein or artery.

10. The method of claim 6, further comprising advancing said catheter with respect to said needle into the vein or artery.

11. The method of claim 6, comprising inserting said needle into the patient where the curved distal surface contacts a surface of the vein or artery at the insertion site and promotes an inward movement of said needle into the vein or artery.

12. A catheter assembly comprising:

a needle having a needle body having a longitudinal dimension with a proximal end and a distal end, a first longitudinal side surface, a second longitudinal side surface opposite said first longitudinal side surface, and a first bevel extending between said first longitudinal side surface and said second longitudinal side surface to define a distal tip at said second longitudinal side surface, said first bevel facing outwardly with respect to said first longitudinal side surface of said needle, a second reverse bevel and a third reverse bevel converging at said distal tip and forming cutting edges between said second reverse bevel and said first bevel, between said third reverse bevel and said first bevel, and a first cutting edge between said second reverse bevel and said third reverse bevel, said cutting edges being oriented radially inward relative to an outer peripheral surface, and an inwardly curved distal surface formed between the second longitudinal side surface of the needle and a proximal end of the first cutting surface such that said cutting edges are configured to cut a surface of a vein or artery to form an opening in said vein or artery until said inwardly curved distal surface contacts the surface of the vein or artery, and then the inwardly curved distal surface is configured to slide through the opening without further cutting the vein or artery, and said inwardly curved distal surface extending between said second longitudinal side surface and said proximal end of the first cutting edge between said second reverse bevel and said third reverse bevel, and said second longitudinal side surface has a notch defining a blood flashback passage opposite said first bevel, said first bevel formed at an angle of 16-22° with respect to the longitudinal dimension of said needle, and said second reverse bevel and third reverse bevel formed at an angle of 75-85° with respect to each other to form said inclined cutting edge;

a catheter positioned on said needle, where said needle is removable from said catheter; and a catheter hub receiving said catheter, said catheter hub having a first longitudinal side surface with a push tab configured for manipulating the catheter assembly by a thumb or finger of a user and a second longitudinal side surface configured without interference from push tabs configured for facing the skin of a patient, and where said first bevel of said needle faces a same side of the second longitudinal side surface of said catheter hub where said distal tip does not contact an inner surface of said catheter when said catheter is advanced over said distal tip.

13. The catheter assembly of claim 12, wherein said catheter is an IV catheter, and where said blood flashback passage in said needle body is in communication with a blood control member, and a guide wire extending through said needle.

14. The catheter assembly of claim 13, wherein said blood flashback passage extends between said needle body and said catheter.

15. The catheter assembly of claim 14, wherein said blood flashback passage is in communication with a lumen in said needle body, and where said catheter hub is connected to said blood control member.

16. The catheter assembly of claim 13, wherein said needle body includes a lumen forming said blood flashback passage and where said catheter hub is coupled to a needle hub connected to said blood control member for receiving blood from said needle.

* * * * *